(12) United States Patent
Goris

(10) Patent No.: US 6,698,888 B2
(45) Date of Patent: Mar. 2, 2004

(54) OPHTHALMIC REFRACTOR HAVING IMPROVED REPEATABILITY OF SCALE ROTATION

(75) Inventor: Christopher Goris, Lancaster, NY (US)

(73) Assignee: Reichert, Inc., Depew, NY (US)

( * ) Notice: Subject to any disclaimer, the term of this patent is extended or adjusted under 35 U.S.C. 154(b) by 84 days.

(21) Appl. No.: 10/136,644

(22) Filed: May 1, 2002

(65) Prior Publication Data

US 2003/0206273 A1 Nov. 6, 2003

(51) Int. Cl.[7] .................................................. A61B 3/02
(52) U.S. Cl. ........................................ 351/233; 351/234
(58) Field of Search ................................ 351/200, 222, 351/227, 228, 229, 230, 231, 233, 234, 235, 236

(56) References Cited

U.S. PATENT DOCUMENTS

| 2,968,213 | A | | 1/1961 | Wright et al. |
| 2,995,065 | A | | 8/1961 | Wright et al. |
| 3,860,330 | A | * | 1/1975 | Persson ........................ 351/235 |
| 4,523,822 | A | * | 6/1985 | Thurston ...................... 351/234 |
| 4,606,624 | A | * | 8/1986 | Wood .......................... 351/234 |
| 4,943,162 | A | * | 7/1990 | Sims ........................... 351/235 |
| 5,104,214 | A | * | 4/1992 | Sims ........................... 351/235 |
| 5,120,124 | A | * | 6/1992 | Sims ........................... 351/235 |
| 5,278,593 | A | * | 1/1994 | Nielsen et al. ............... 351/235 |
| 5,281,984 | A | * | 1/1994 | Burton et al. ................ 351/234 |
| 5,617,157 | A | * | 4/1997 | Shalon et al. ................ 351/233 |
| 5,812,241 | A | * | 9/1998 | Doms et al. .................. 351/235 |

* cited by examiner

Primary Examiner—George Manuel
Assistant Examiner—John R Sanders
(74) Attorney, Agent, or Firm—Hodgson Russ LLP

(57) ABSTRACT

A subjective ophthalmic refractor of a type comprising a ring-shaped cylinder power scale having an internal gear actuated by a scale drive gear connected to a cylinder power adjustment knob of the refractor is improved by providing a bearing insert within the cylinder power scale. The bearing insert includes radially and axially facing annular bearing surfaces extending about a substantial portion of the scale, and a cut-out region allowing space necessary for the scale drive gear.

21 Claims, 3 Drawing Sheets

OPHTHALMIC REFRACTOR HAVING IMPROVED REPEATABILITY OF SCALE ROTATION

FIELD OF THE INVENTION

The present invention relates generally to ophthalmic instruments, and more particularly to subjective ophthalmic refractors for evaluating refractive characteristics of a patient's eye.

BACKGROUND OF THE INVENTION

A subjective ophthalmic refractor typically comprises left-eye and right-eye batteries each having a defined viewing path along which an operator may selectively introduce combinations of testing lenses having known refractive properties. During examination, the patient is positioned in a darkened room with his or her eyes aligned to view a projected target chart along the viewing paths defined by the left-eye and right-eye batteries. The operator then performs well-known refracting procedures, including refraction using astigmatic charts and the Jackson cross-cylinder test. A goal of the examination procedure is to determine the sphere power, cylinder power, and cylinder axis of each eye so that a suitable pair of corrective lenses may be prescribed.

U.S. Pat. No. 2,968,213 describes an ophthalmic refractor of the prior art. FIG. 5 of the '213 patent is an exploded view illustrating the internal components of a left eye lens battery, and serves to illustrate a lonstanding arrangement for mechanically coupling a pair of rotatable cylinder lens carriers 8 and 9 and an associated ring-shaped cylinder power scale 50 of the battery to an adjustment knob 20 used by the operator to set a chosen cylinder power in the viewing path of the battery. As can be seen at FIG. 1 of the '213 patent, the indicia on scale 50 can be viewed by the operator through an opening 52 in the battery housing. Typically, the indicia are numerical cylinder power values from 0 to 6.00 diopters in quarter-diopter increments, and are angularly spaced at regular angular increments about a central axis of the ring-shaped scale. The mechanical interconnections from knob 20, through cylinder power scale 50, to the lens carriers 8 and 9 are designed such that rotation of knob 20 positions two lenses (or a lens and an empty lens cell), one from lens carrier 8 and one from lens carrier 9, in series in the viewing path to produce a resultant cylinder power. Lens carrier 8 is a "weak" cylinder lens carrier having, for example, a blank lens cell (zero power) and four cylinder lenses ranging in power from 0.25 diopters to 1.00 diopters at quarter diopter increments. Meanwhile, lens carrier 9 is a "strong" cylinder lens carrier having, for example, a blank lens cell (zero power) and four cylinder lenses ranging in power from 1.25 diopters to 5.00 diopters at 1.25-diopter increments. Consequently, by indexing the weak cylinder lens carrier 8 five times for every one index movement of strong cylinder lens carrier 9, a cylinder power range of 0.00 diopters to 6.00 diopters at quarter-diopter increments is possible in agreement with the indicia on scale 50.

With continued reference to U.S. Pat. No. 2,968,213, it will be seen that adjustment knob 20 drives a shaft 21 having at its opposite end a dual gear comprising a small front gear 23 and a larger rear gear 25. Larger gear 25 meshes with a gear 31 fixedly connected to the hub of a driver plate 27, whereby rotation of knob 20 and larger gear 25 produces counter-rotation of driver plate 27. As driver plate 27 rotates about its axis, four short pegs 39a–39d on the driver plate successively engage weak cylinder lens carrier 8 to index only the weak lens carrier, and a fifth longer peg 40 engages both the weak and strong lens carriers 8 and 9 to index both carriers, in the manner of a Geneva mechanism. A spring-biased roller 48' cooperates with five circumferential detents 53' in driver plate 27 to allow the operator to feel each index position at adjustment knob 20.

Meanwhile, small front gear 23 meshes with internal gear teeth on ring-shaped scale 50 to rotate the scale in coordination with the indexing of cylinder lens carriers 8 and 9, whereby an appropriate cylinder power value marked on the scale appears through opening 52. Scale 50 is constrained both radially and axially by three bearings 56 located at respective positions about the circumference of scale 50. Each bearing 56 includes a low friction circular base slidably contacted by the marked side of scale 50, and a stepped cylindrical retainer post fastened coaxially along with the base to the refractor housing to define a gap through which the circumferential outer edge of scale 50 passes. Due to space limitations within the refractor housing, bearings 56 are not spaced at regular 120° angular intervals about the rotational axis of scale 50. This reliable arrangement for rotatably supporting and positioning scale 50 has heretofore remained unimproved, despite the existence of certain drawbacks with respect thereto. In particular, bearings 56 are difficult to adjust during assembly, the tolerances of the retainer posts and scale 50 cause misalignment of indicia in view opening 52, and the localized support at irregular angular intervals creates a poor fit. Consequently, the rotation of adjustment knob 20 does not feel as smooth and uniform to the user as would be desired.

SUMMARY OF THE INVENTION

Therefore, it is an object of the present invention to provide an improved arrangement for mounting a rotatable ring-shaped scale in an ophthalmic refractor that allows for easy assembly.

It is another object of the present invention to provide an improved arrangement for mounting a rotatable ring-shaped scale in an ophthalmic refractor that achieves a smoother adjustment knob feel to the user without introducing more demanding tolerances in critical components.

It is a further object of the present invention to provide an improved arrangement for mounting a rotatable ring-shaped scale in an ophthalmic refractor that reduces the overall number of bearing components.

In furtherance of these and other objects, an ophthalmic refractor of a type comprising a ring-shaped cylinder power scale having an internal gear, a rotatable cylinder power adjustment knob, and a scale drive gear fixed for rotation with the adjustment knob and meshing with the internal gear of the cylinder power scale is improved with respect to the manner in which the cylinder power scale is supported and located. In particular, a prior art arrangement of three bearing posts irregularly-spaced at points on the outer circumference of the cylinder power scale is replaced by a generally circular bearing insert located in the interior of the scale and mounted on an existing axle stem fixed to the an eye battery housing of the refractor. The cylinder power scale is confined against radially directed movement by a first retaining surface of the bearing insert that faces in a radially outward direction for engaging the crests of the scale's internal gear teeth. The cylinder power scale is confined against axially directed movement by a second retaining surface defined by a circumferential lip on the bearing insert, and by a low-friction bearing plate fixed to the eye battery housing. A U-shaped cut-out region in the bearing insert allows space for the scale drive gear. The arrangement of the present invention provides more uniformly and extensively distributed bearing surfaces for guiding the gear-driven rotation of the cylinder power scale in an improved manner.

BRIEF DESCRIPTION OF THE DRAWING

The nature and mode of operation of the present invention will now be more fully described in the following detailed description of the invention taken with the accompanying drawing figures, in which.

DETAILED DESCRIPTION OF THE INVENTION

Figure 1:
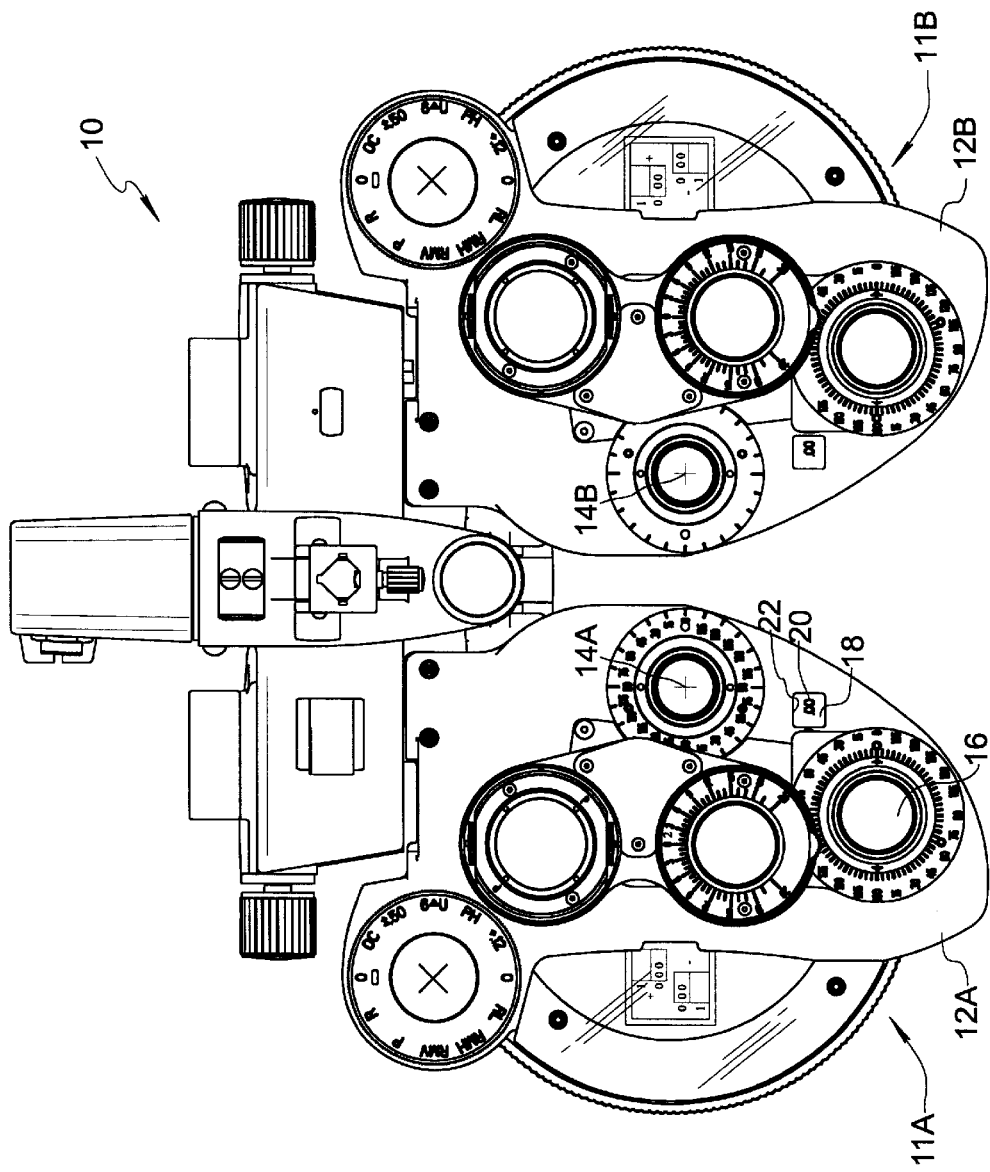
FIG. 1 is a front elevational view of an ophthalmic refractor formed in accordance with a preferred embodiment of the present invention.

FIG. 1 shows a subjective ophthalmic refractor 10 formed in accordance with a preferred embodiment of the present invention. Ophthalmic refractor 10 is of a type well-known in the art of ophthalmic instruments in that it generally comprises a right eye battery 11A and a left eye battery 11B that are mirror images of each other. Eye batteries 11A and 11B comprise respective housings 12A and 12B and respective viewing paths 14A and 14B along which a patient facing a back side of the instrument gazes during examination. The construction and operation of ophthalmic refractor 10 are generally and substantially as taught in U.S. Pat. Nos. 2,968,213 and 2,995,065, both these patents being incorporated herein by reference.

The present invention relates to an improvement involving a cylinder power adjustment system found in each eye battery, 11A and 11B. For sake of simplicity, the invention is described with respect to right eye battery 11A only, it being understood that left eye battery 11B is a mirror image of right eye battery 11A. Battery 11A comprises a cylinder power adjustment knob 16, a cylinder power scale 18 having numerical indicia 20 indicative of a cylinder power introduced in viewing path 14A, and an opening 22 in battery housing 12A for allowing an appropriate power value on scale 18 to be viewed by an ophthalmic practitioner.

Figure 2:
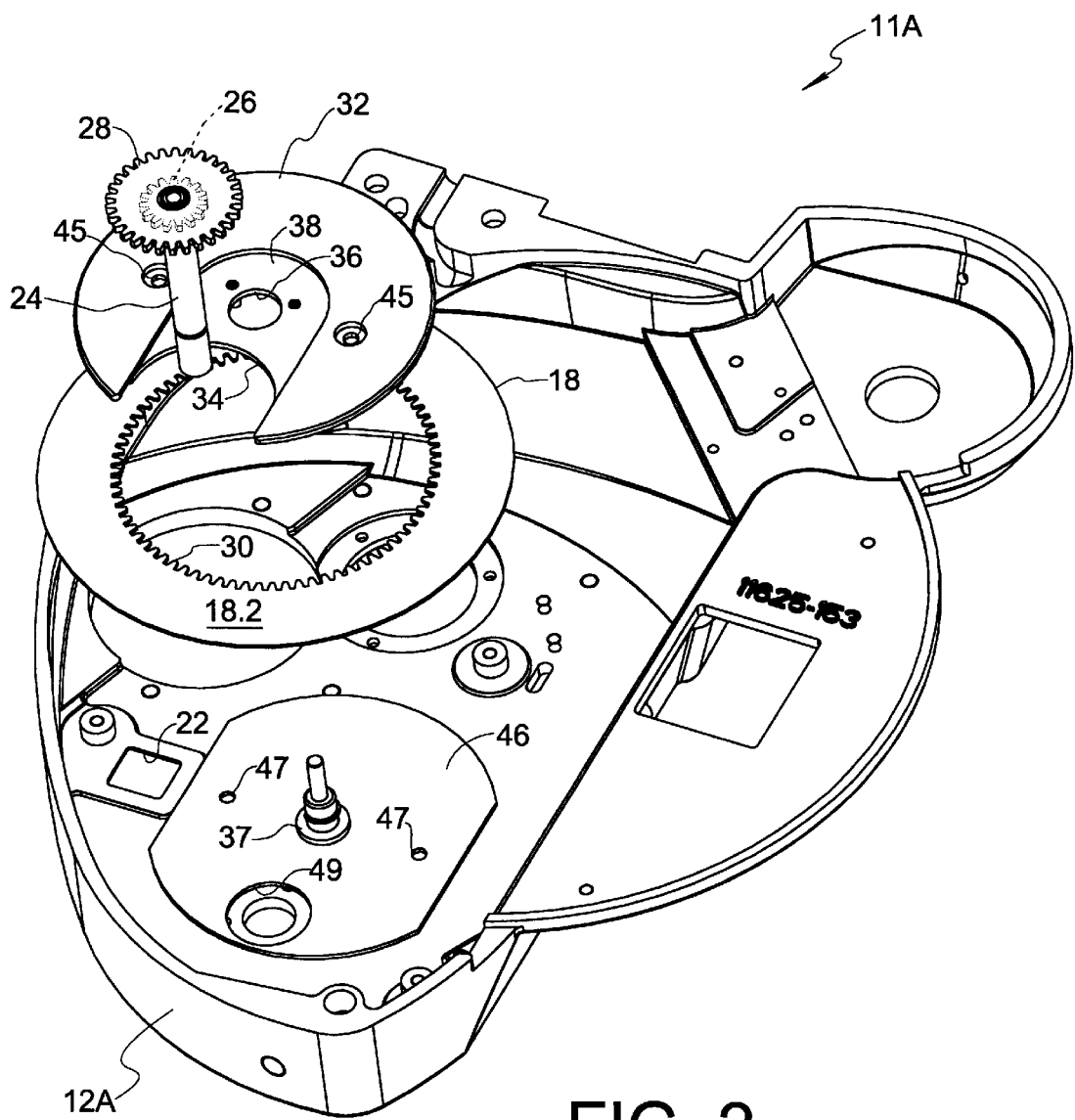
FIG. 2 is an exploded perspective view of an eye battery of the ophthalmic refractor shown in FIG. 1.
Figure 3:
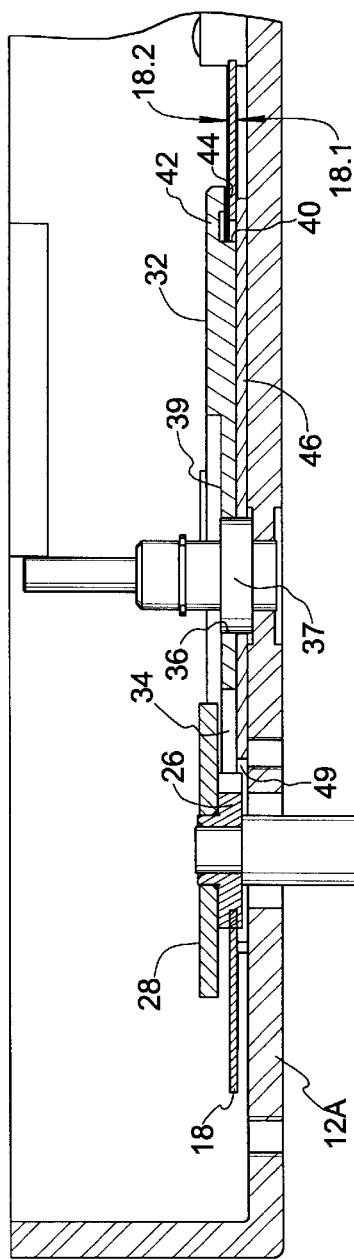
FIG. 3 is an enlarged cross-sectional view of a portion of the eye battery shown in FIG. 2.
Figure 4:
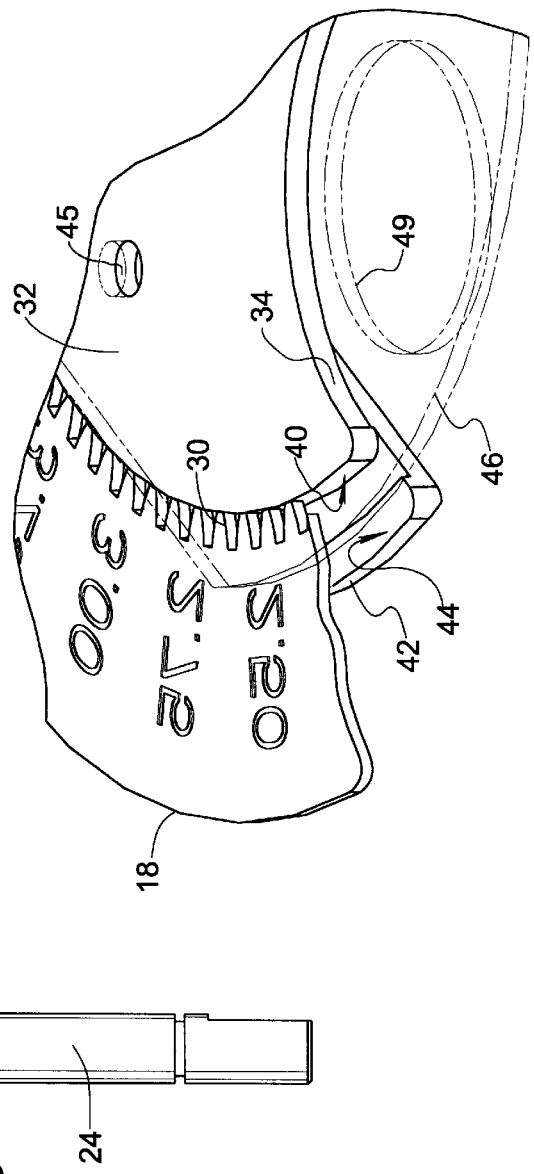
FIG. 4 is an enlarged perspective view showing a portion of a cylinder power scale of the eye battery and a bearing insert therefor.

Referring also now to FIGS. 2 through 4 of the drawings, adjustment knob 16 is fixed on a shaft 24 having at its opposite end a dual gear comprising a small front gear 26 and a larger rear gear 28. Larger gear 28 transmits torque to a Geneva mechanism for indexing a pair of cylinder lens carriers (not shown) as described in referenced U.S. Pat. No. 2,968,213. Small gear 26 meshes with an internal gear 30 of cylinder power scale 18 to rotate the cylinder power scale simultaneously and in concert with the rotational indexing of the cylinder lens carriers. Cylinder power scale 18 includes a frontward-facing first side 18.1 on which indicia 20 are marked or applied, and a rearward-facing second side 18.2.

In accordance with a preferred embodiment of the present invention, eye battery 11A comprises a bearing insert 32 located internally with respect to ring-shaped cylinder power scale 18. Bearing insert 32 is generally circular in shape and includes a U-shaped cut-out region 34 providing space to accommodate small gear 26 and larger gear 28, a central aperture 36 allowing the insert to be mounted on an existing stem 37 defining a rotational axis for a pegged driver plate (not shown) of the Geneva mechanism, and a recessed region 39 surrounding central aperture 36 and adjacent to cut-out region 34 for accommodating a gear (not shown) fixed to the pegged driver plate. As best seen in FIG. 4, bearing insert 32 comprises a first retaining surface 40 facing in a radially outward direction for engaging the crests of gear teeth of internal gear 30, thereby confining scale 18 against radially directed movement. FIG. 4 also shows a circumferential lip 42 of bearing insert 32 that serves to define a forwardly-facing second retaining surface 44 for confining scale 18 against axially directed movement. The radial reach of lip 42 is chosen such that second retaining surface 44 is spaced from, but remains close to, internal gear 30. Bearing insert also includes a pair of fastener holes 45.

Eye battery 11A further comprises a bearing plate 46 fixed relative to housing 12A and arranged in surface-to-surface contact with a radially inner portion of first side 18.1 of cylinder power scale 18. Bearing plate 46 is preferably formed of ultra high molecular weight (UHMW) plastic or other low friction material so as to minimize a coefficient of friction between the surface of bearing plate 46 and first side 18.1 of scale 18. The pair of fastener holes 45 through bearing insert 32 are alignable with a pair of fastener holes 47 provided through bearing plate 46, whereby the bearing insert 32 and bearing plate 46 can be fixed to housing 12A by a pair of fasteners (not shown).

As will be appreciated from the foregoing description, the irregular three-point bearing arrangement on the outside of the cylinder power scale according to the prior art is replaced by an internal bearing arrangement providing first and second retaining surfaces 40 and 44 distributed uniformly about a rotational axis of the scale through an included angle limited by the width of cut-out region 34 in bearing insert 32. In accordance with the present invention, the included angle of first and second retaining surfaces 40 and 44 about a central axis of bearing insert 32 is greater than 180° and preferably as large as possible. In a current commercial embodiment, the included angle through which first and second retaining surfaces 40 and 44 continuously extend is approximately 300°. The improved bearing arrangement of the present invention eliminates binding, uneven frictional resistance, and assembly problems associated with the prior art to provide repeatably accurate rotation of cylinder power scale 18 throughout the lifetime of the instrument.

What is claimed is:

1. An ophthalmic refractor comprising:
   a housing;
   a viewing path through said housing;
   a lens carrier mounted in said housing, said lens carrier holding a plurality of lenses;
   a rotatable adjustment knob operatively connected to said lens carrier for enabling a user to selectively position a chosen lens in said viewing path;
   a ring-shaped scale including a first side having angularly spaced indicia for indicating an optical parameter related to said chosen lens and a second side opposite said first side, said scale having an internal gear;
   a scale drive gear fixed for rotation with said adjustment knob and meshing with said internal gear of said scale to rotate said scale upon rotation of said adjustment knob; and
   a bearing insert located internally with respect to said ring-shaped scale, said bearing insert acting to confine said ring-shaped scale in radial and axial directions.

2. The ophthalmic refractor according to claim 1, wherein said bearing insert is generally circular in shape and includes a cut-out region for accommodating said scale drive gear.

3. The ophthalmic refractor according to claim 2, wherein said bearing insert includes a first retaining surface for confining said scale against radially directed movement and a second retaining surface for confining said scale against axially directed movement.

4. The ophthalmic refractor according to claim 3, wherein said first retaining surface extends circumferentially about a central axis of said bearing insert continuously through an included angle greater than 180°.

5. The ophthalmic refractor according to claim 4, wherein said included angle is approximately 300°.

6. The ophthalmic refractor according to claim 3, wherein said second retaining surface extends circumferentially about a central axis of said bearing insert continuously through an included angle greater than 180°.

7. The ophthalmic refractor according to claim 6, wherein said included angle is approximately 300°.

8. The ophthalmic refractor according to claim 3, wherein said second retaining surface is defined by a circumferential lip on said bearing insert, wherein said second retaining surface is arranged to face said second side of said scale at a radial location spaced from a radial location of said internal gear.

9. The ophthalmic refractor according to claim 2, wherein said bearing insert includes a recessed region surrounding a central axis thereof and adjacent to said cut-out region.

10. The ophthalmic refractor according to claim 1, further comprising a bearing plate fixed relative to said housing and in surface-to-surface contact with said first side of said scale.

11. The ophthalmic refractor according to claim 10, wherein said bearing plate is formed of ultra-high molecular weight plastic.

12. The ophthalmic refractor according to claim 1, wherein said scale reports a selected cylinder power.

13. In an ophthalmic refractor of a type comprising a ring-shaped cylinder power scale having an internal gear, a rotatable cylinder power adjustment knob, and a scale drive gear fixed for rotation with said adjustment knob and meshing with said internal gear of said cylinder power scale, the improvement comprising:

a bearing insert located internally with respect to said ring-shaped cylinder power scale, said bearing insert acting to confine said cylinder power scale in radial and axial directions.

14. The improvement according to claim 13, wherein said bearing insert is generally circular in shape and includes a cut-out region for accommodating said scale drive gear.

15. The improvement according to claim 14, wherein said bearing insert includes a first retaining surface for confining said cylinder power scale against radially directed movement and a second retaining surface for confining said cylinder power scale against axially directed movement.

16. The improvement according to claim 15, wherein said first retaining surface extends circumferentially about a central axis of said bearing insert continuously through an included angle greater than 180°.

17. The improvement according to claim 16, wherein said included angle is approximately 300°.

18. The improvement according to claim 15, wherein said second retaining surface extends circumferentially about a central axis of said bearing insert continuously through an included angle greater than 180°.

19. The improvement according to claim 18, wherein said included angle is approximately 300°.

20. The improvement according to claim 15, wherein said second retaining surface is defined by a circumferential lip on said bearing insert, wherein said second retaining surface is arranged to face said second side of said scale at a radial location spaced from a radial location of said internal gear.

21. The improvement according to claim 14, wherein said bearing insert includes a recessed region surrounding a central axis thereof and adjacent to said cut-out region.

* * * * *